(12) United States Patent
Cebe (10) Patent No.: US 11,617,669 B2
(45) Date of Patent: Apr. 4, 2023

(54) DEVICE FOR THE EXTERNAL APPLICATION OF A LOCAL COMPRESSIVE FORCE BELOW THE COSTAL ARCH OF A PATIENT TO REDUCE THE STOMACH VOLUME

(71) Applicant: Fevzi Cebe, Cologne (DE)

(72) Inventor: Fevzi Cebe, Cologne (DE)

( * ) Notice: Subject to any disclaimer, the term of this patent is extended or adjusted under 35 U.S.C. 154(b) by 943 days.

(21) Appl. No.: 16/467,904

(22) PCT Filed: Dec. 7, 2017

(86) PCT No.: PCT/EP2017/081827
§ 371 (c)(1),
(2) Date: Jun. 7, 2019

(87) PCT Pub. No.: WO2018/104450
PCT Pub. Date: Jun. 14, 2018

(65) Prior Publication Data
US 2020/0060857 A1 Feb. 27, 2020

(30) Foreign Application Priority Data
Dec. 8, 2016 (DE) .......................... 102016015072.6

(51) Int. Cl.
*A61F 5/00* (2006.01)
*A61B 5/00* (2006.01)
*A61F 5/03* (2006.01)
(52) U.S. Cl.
CPC .......... *A61F 5/0009* (2013.01); *A61B 5/0017* (2013.01); *A61B 5/4836* (2013.01); *A61F 5/03* (2013.01)

(58) Field of Classification Search
CPC .. A61F 5/0009; A61F 5/03; A61F 5/24; A61F 5/26; A61F 5/28; A61F 5/30;
(Continued)

(56) References Cited

U.S. PATENT DOCUMENTS 2,671,899 A * 3/1954 Kroger ................. A61F 5/0009
450/94
3,578,773 A * 5/1971 Schultz ..................... A61F 5/24
602/19
(Continued)

FOREIGN PATENT DOCUMENTS

DE        3500078 A  *  7/1985    ........... A61F 5/0009
DE        3500078 A1     7/1985
(Continued)

OTHER PUBLICATIONS

PCT, International Search Report cited in PCT/EP2017/081827, completed Mar. 9, 2018.

*Primary Examiner* — Tarla R Patel
(74) *Attorney, Agent, or Firm* — Moore & Van Allen, PLLC; Henry B. Ward, III (57) ABSTRACT

A device (10) for externally applying a local compressive force below the costal arch (R) of a patient for reducing the stomach volume, comprising—an elastic belt (10) that is placeable, under tensile stress, around the upper body of a patient in the area of the costal arch (R), and—a pressure body (24) that is attachable to the elastic belt (12) and designed in such a way that the pressure body exerts a compressive force on the stomach inside the patient according to the tensile stress of the elastic belt (12), wherein the geometry of the pressure body (24) is adapted to the anatomy of the human costal arch and fits snugly therein.

18 Claims, 6 Drawing Sheets

(58) Field of Classification Search
CPC ..... A61F 5/32; A61F 5/34; A61F 5/37; A61B 5/0017; A61B 5/4836; A61B 5/0036; A61B 5/0053; A61B 5/0055; A61B 5/0057

See application file for complete search history.

(56) References Cited

U.S. PATENT DOCUMENTS

| | | | | |
|---|---|---|---|---|
| 4,411,258 A * | 10/1983 | Pujals, Jr. | ............... | A61H 39/04 |
| | | | | 601/134 |
| 4,592,342 A * | 6/1986 | Salmasian | ................. | A61F 5/30 |
| | | | | 604/909 |
| 4,991,573 A * | 2/1991 | Miller | ...................... | A61F 5/028 |
| | | | | 128/99.1 |
| 5,062,414 A * | 11/1991 | Grim | ....................... | A61F 5/028 |
| | | | | 128/DIG. 20 |
| 7,264,600 B2 * | 9/2007 | Brinston, Sr. | ......... | A61H 9/0078 |
| | | | | 601/75 |

FOREIGN PATENT DOCUMENTS

| | | | | | |
|---|---|---|---|---|---|
| DE | 19822221 A1 * | 11/1999 | ........... | A61F 5/0009 |
| DE | 19822221 A1 | 11/1999 | | |
| DE | 10207887 A1 * | 9/2003 | ........... | A61H 9/0078 |
| DE | 10207887 A1 | 9/2003 | | |
| WO | 2010042080 A1 | 4/2010 | | |

\* cited by examiner

DEVICE FOR THE EXTERNAL APPLICATION OF A LOCAL COMPRESSIVE FORCE BELOW THE COSTAL ARCH OF A PATIENT TO REDUCE THE STOMACH VOLUME

FIELD OF THE INVENTION

The present invention relates to a device for externally applying a local compressive force below the costal arch of a patient for reducing the stomach volume.

BACKGROUND OF THE INVENTION

The treatment of overweight persons affected by metabolic disorders or obesity is gaining increasing importance. One approach to this treatment is to reduce the stomach volume of a patient. For this purpose, in addition to dietary or medicinal treatment approaches there are in particular invasive or surgical forms of treatment, such as application of a gastric band, surgical stomach reduction, or introduction of a gastric balloon.

The surgical forms of treatment generally quickly result in a certain level of success, at least temporarily, but for patients who have a tendency to repeatedly become overweight, these procedures generally can be performed only a few times, not as often as desired. For example, a stomach reduction may generally be performed only once on a patient. In addition to this drawback, surgical forms of treatment involve the known side effects of a surgical procedure, so that these forms of treatment are not suitable for all patients. Furthermore, surgical procedures are costly and involve risk to the patient.

Dietary treatment approaches are often lengthy, and require significant discipline by the affected patients. For this reason, they are frequently not successful since they require that the patient alter his/her lifestyle.

Medicinal treatment approaches often have significant side effects that impose unnecessary stress on the patient's body.

Therefore, there is a need for conservative, i.e., nonsurgical, and also nonmedicinal treatment approaches for overweight persons.

Various devices are already known from the prior art with the aim of using a conservative approach to reduce the stomach volume of a patient from the outside.

U.S. Pat. No. 7,264,600 B2 describes an active belt for weight control. The active belt may be used to inflate air cushions in a targeted manner. In addition, a type of massage function is described.

DE 102 07 887 A1 discloses a device via which external pressure may be pneumatically or hydraulically applied in the stomach area.

U.S. Pat. No. 2,671,899 discloses a device for increasing the pressure in the stomach area of a patient, with provision of a hollow body mounted on a belt, the hollow body being provided with individual vent openings and intended to exert pressure on the stomach area.

DE 35 00 078 A1 describes numerous design variants for an abdominal belt for applying pressure to the stomach area of a patient.

WO 2010/042080 A1 describes a corset, which on the one hand is intended to improve the physical appearance of a patient by shaping, and on the other hand to curb the appetite of a patient, by targeted application of pressure to the stomach area.

DE 198 22 221 A1 discloses a further device for applying pressure to the stomach area of a patient, using various padding elements.

BRIEF SUMMARY OF THE INVENTION

The object of the present invention is to provide a device that is suitable for reducing the volume of the stomach of a patient.

This object is achieved by a device for externally applying a local compressive force below the costal arch of a patient for reducing the stomach volume, the device comprising:
  an elastic belt that is placeable, under tensile stress, around the upper body of a patient in the area of the costal arch, and
  a pressure body that is mounted on or attachable to the elastic belt and designed in such a way that the pressure body exerts an external compressive force on the stomach inside the patient according to the tensile stress of the elastic belt,
wherein the geometry of the pressure body is adapted to the anatomy of the human costal arch and fits snugly therein.

The inventor has recognized that it is possible in principle to reduce the stomach volume of a patient on a sustained basis by externally applying a compressive force to the body of the patient in the area of the stomach, thus reducing the patient's feeling of hunger. To continuously apply such a compressive force to the body of the patient in the area of the stomach, the elastic belt, which is under tensile stress, is placed around the upper body of the patient in the area of the costal arch. The compressive force exerted on the upper body of the patient in the radial direction by the elastic tensile stress of the belt is concentrated on the stomach area, at least in part, at specific points or locally via the pressure body on the stomach area, and a compressive force is thus continuously exerted on the stomach area of the patient. According to the invention, this is advantageously achieved in particular in that the geometry of the pressure body is adapted to the costal arch of the patient and fits snugly therein, so that the compressive force is applied at that location. In other words, according to the invention the pressure body is designed in the shape of a negative imprint of the costal arch. The pressure body, without major losses of compressive force on the costal arch, thus results in compression of the upper abdomen in the area of the epigastrium (stomach), as the result of which the air in the stomach is compressed and expelled, and the stomach volume is reduced on a sustained basis and restricted. In this regard, it should be noted that the organs in the abdominal cavity are situated in an air-free space (vacuum), and the stomach and the intestine are the only organs that can contain air. A pressure that is applied to the abdominal cavity is thus transmitted directly to the stomach and the intestine, resulting in the volume reduction at the desired location.

Over time, by use of the device according to the invention it is possible to achieve a sustained, constant volume reduction by moderate but continuous compression of the stomach, which reduces the feeling of hunger and affects the eating behavior of the patient. The device according to the invention may thus be used to achieve a reduction in the stomach volume conservatively, i.e., without surgical or medicinal intervention, so that the patient feels less hungry, and over time his/her excess weight is reduced due to less food intake.

According to one embodiment of the invention, it may be provided that the elastic belt is closed or designed in the form of an at least partially elastic band, which in the area of its ends may be joined together via connecting means to adjust its effective length around the upper body of the patient. When the belt has a closed design, it is preferably offered in various sizes in order to be usable by patients having different girths. However, an open, band-shaped belt is preferably used that is closeable at its ends via connecting means.

In this regard, it may be provided that the connecting means are designed in the form of a hook and loop fastener, preferably with a flat loop area provided on one end and a flat hook area provided on the other end, or with the connecting means designed in the form of at least one adjustable closure element, such as at least one belt-buckle connection or a twist lock mechanism, latching mechanism, or the like. The belt may thus be adapted to patients as desired, preferably with various belt lengths offered as basic sizes.

One refinement of the invention provides that the pressure body is designed in the form of a flat, flexible pressure body. The pressure body may be designed in particular in the form of a rubber, plastic, or silicone body. As stated at the outset, it is crucial that the pressure body is configured in such a way that it is suitable for engaging below the costal arch, i.e., in such a way that the pressure body, via which the compressive force is exerted on the stomach area via the skin of the patient, can engage with the stomach area below the costal arch. The desired compressive force may thus be exerted on the stomach area in a targeted manner, thus reducing the stomach volume on a sustained basis in a conservative manner.

In this regard, one refinement of the invention provides that the pressure body is designed in the shape of a rounded polygon, in particular a rounded triangle, an ellipse, or an oval. Depending on the anatomy, age, and state of health, a suitable geometry for the pressure body may be selected based on the patient.

According to one advantageous refinement of the invention, the pressure body is designed with an elevation area having an inverted V shape, and having its greatest material thickness in the area of the vertex of the V. The V-shaped elevation area, with its highest elevation in the area of the vertex of the V, anatomically fits into the costal arch, and provides the maximum application of pressure at the area of its highest elevation (epigastrium), ideally at or in the area of the solar plexus of the patient. The elevation area along the legs of the V increases the concentration of pressure in the upper abdomen.

To avoid shifting of the pressure body on the patient and to increase the wearing comfort, according to one refinement of the invention it may be provided that the surface of the pressure body contacting the patient is provided with protruding knobs. As the result of this measure, the pressure body remains in its intended position on the patient. In addition, a certain amount of air circulation is possible in the area of the pressure body, even when the device according to the invention is worn continuously, which increases the wearing comfort.

Furthermore, according to one refinement of the invention it may be provided that fastening means, in particular a loop area or a hook area, are provided on the rear side of the pressure body. In this way the pressure body may be fixed to the belt, or, as described in greater detail below, fixed to an additional pressure pad situated between the belt and the pressure body. As an alternative to a hook and loop fastener, fastening means such as buttons, pushbuttons, latching elements, form-fit elements, magnets, or the like may be provided.

One refinement of the invention provides that a pressure pad is provided between the pressure body and an inner side of the belt intended to contact the patient. When the geometry of this pressure pad is appropriately selected, such an additional arrangement of a pressure pad, also referred to as a "pelotte" in technical jargon, allows application of the compressive force at specific points or over a flat surface, corresponding to the anatomy of the patient.

For reasons of wearing comfort, there are limits to the stiffness of the pressure body. Therefore, in the design of the pressure body, which makes direct contact with the skin of the patient, attention must be paid to skin tolerability and the avoidance of unpleasant points of pressure or friction, which may result in skin irritation. The pressure body is preferably provided with a skin-friendly coating or a cover, in particular made of a cleanable or hygienic textile material.

However, the pressure pad, due to the fact that it does not come into direct contact with the skin of the patient, may be made of a fairly hard material, such as a dimensionally stable, preferably elastic, material, preferably made of rubber, plastic, or silicone. The pressure pad may also be provided with a coating or a cleanable cover. However, the geometry of the pressure pad may be coordinated in particular with the geometry of the desired target area in which the compressive force is to be exerted on the patient in order to reduce the stomach volume. In addition, it may be provided that the pressure body is covered with a looped material, the looped material being formed directly on the pressure body or designed as a replaceable fabric pocket that accommodates the pressure body.

With regard to the geometry of the pressure pad, it may be provided that the pressure pad has a convex, i.e., outwardly curved, shape at least on one side, wherein the pressure pad may in particular have a rectangular, rounded rectangular, elliptical, or oval cross section. As indicated above, pressure pads having different geometries and hardnesses may be used, depending on the anatomical characteristics of the patient and the treatment situation.

For fixing the pressure pad between the belt and the pressure body, one refinement of the invention provides that the pressure pad has a fastening means, in particular with a loop area or a hook area, on its side facing the belt and on its side facing the pressure body. Buttons, pushbuttons, latching elements, form-fit elements, magnets, or the like may be provided for fixing the pressure pad as an alternative to fastening via a hook and loop fastener.

One refinement of the invention provides that the belt is attachable in an area in which the pressure body is reinforced by a dimensionally stable reinforcement element, optionally by means of the above-described pressure pad. By use of such a reinforcement element, for example the pressure pad and/or the pressure body may be stabilized in their/its position relative to the patient, thus ensuring the continuous application of a compressive force in an even more reliable manner. In this regard, it may be provided that the area in which the pressure body is attachable, optionally by means of the pressure pad, is situated in a middle section or in an end area of the belt. Depending on the configuration, this may allow the belt to be closed, for example, in a back area of the patient or in the chest area of the patient.

For example, in one design variant of the invention the reinforcement element may have a rounded vertex area that is situated off-center, preferably in an area of one-third the total length of the reinforcement element, the reinforcement element in its vertex area preferably having an opening angle of 170° to 120°, most preferably an opening angle of approximately 150°. It is thus possible to align the vertex area, in coordination with the pressure body for maximum application of compressive force, with the area of maximum material thickness or maximum elevation of the body.

However, this design of the reinforcement element also allows variable utilization of the reinforcement element in different arrangements relative to the pressure body in order to apply less or more pressure to the stomach area, depending on the needs of the patient. It may be provided that the reinforcement element is selectively providable in a convex or concave arrangement relative to the pressure body, and/or selectively providable with its vertex area near or far from a maximum material thickness of the pressure body. In other words, via the reinforcement element it is possible, depending on the orientation of the reinforcement element, to provide more or less support for the compressive force that is applied to the stomach area by the pressure body.

One refinement of the invention preferably provides that the belt has a recess or retaining pocket for accommodating the reinforcement element. This ensures that the position of the reinforcement element remains stable in the belt.

Furthermore, one refinement of the invention provides that the reinforcement element is formed by a curved, arch-shaped reinforcement strip that is provided with two end areas that protrude with respect to a middle area, the reinforcement element being accommodated in the belt or mounted thereon in such a way that the two end areas protrude toward the patient. The reinforcement strip may, for example, be a metal strip or a stable plastic strip made of a thermoplastic material or the like.

One refinement of the invention provides that at least one sensor for detecting patient parameters, in particular a sensor for detecting the pulse and/or heart rate and/or blood pressure and/or blood sugar and/or respiratory rate and/or body temperature and/or fat percentage and/or water percentage and/or muscle percentage and/or body mass index or the like, is provided in the belt in an area that is in contact with the skin of the patient, in particular in the pressure body. Such sensors may include electrodes that come into direct contact with the skin of the patient. These sensors may be powered, for example, by a shared power supply unit in the form of a battery. The sensors may be coupled to an evaluation unit, for example a smart phone or a smart watch or a computer or a tablet or electronic scales, or some other electronic evaluation unit, via a cabled or cable-free interface, for example via IR, Bluetooth, Wi-Fi, or a mobile radio connection. It is also possible according to the invention to remotely monitor patient data and patient parameters directly via a mobile radio interface situated in or on the belt, or by connecting a transmitter to a smart phone or a smart watch, for example.

BRIEF DESCRIPTION OF THE SEVERAL VIEWS OF THE DRAWINGS

Various embodiments of the invention are explained below by way of example, with reference to the accompanying figures, which show the following.

DETAILED DESCRIPTION OF THE INVENTION

Figure 1:
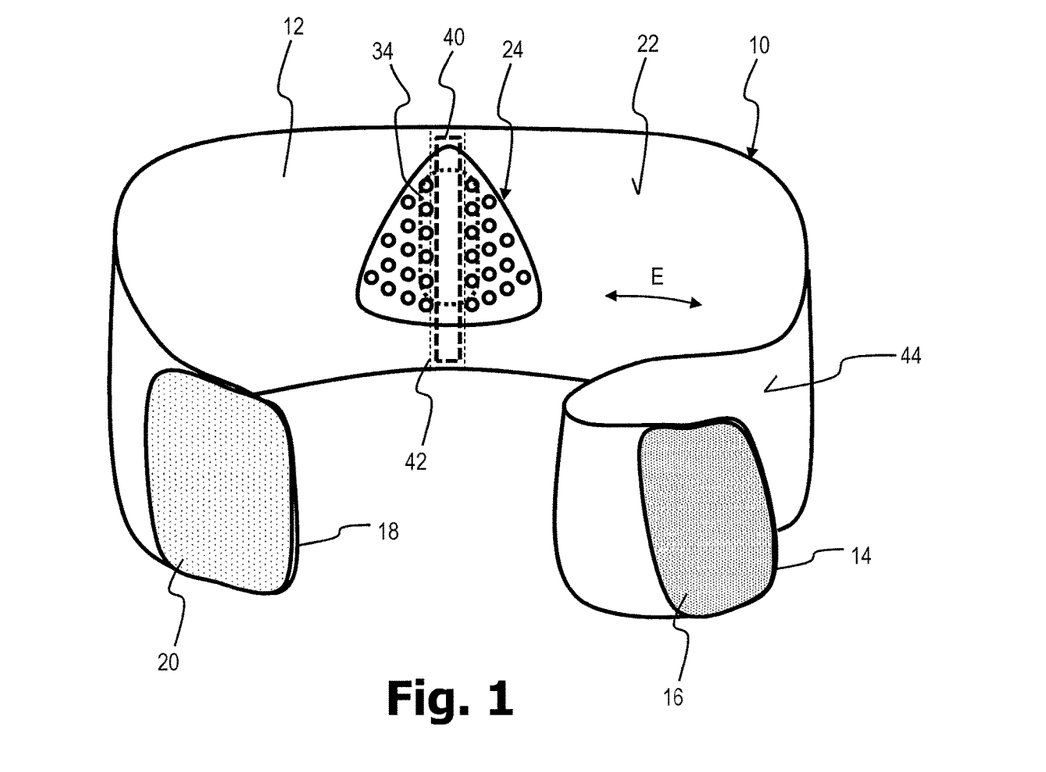
FIG. 1 shows a schematic perspective view of a device according to the invention, according to a first embodiment.

FIG. 1 shows a perspective illustration of a device according to the present invention, denoted overall by reference numeral 10. The device 10 includes a belt 12 made of an elastic material that is elastically stretchable along its longitudinal direction according to the arrow E. On one end 14 the belt 12 has a flat hook and loop fastener panel 16 that is provided with hooks. On its other end 18 the belt 12 has a flat hook and loop fastener panel 20 that is designed as loops, and for closing the belt 12 around the upper body of a patient, the hooks of the panel 16 may be engaged with the loops of the panel 20 with variable tightness in order to provide a secure hold even under elastic tensile stress.

Figure 2:
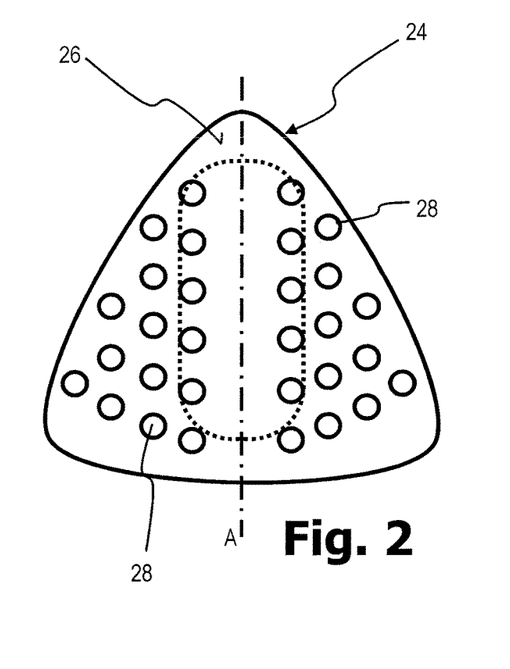
FIG. 2 shows an enlarged front view of the triangular pressure body according to the first embodiment of the invention.

In its middle area, the belt 12 has a pressure body 24, designed in the shape of a triangle with rounded corners, on its inner side 22. The pressure body 24 is illustrated in a front view in FIG. 2, in a top view in FIG. 3, and in a rear view in FIG. 4. The pressure body 24 is manufactured from a dimensionally stable but deformable rubber material, and at least on its front side 26 is covered with a hygienic cover material that is easy to clean. In addition, the pressure body 24 on its front side 26 has a series of rounded, knoblike projections 28 that are in particular arranged in uniform patterns on each side of an imaginary center axis A. No such projections 28 are provided in the area around the center axis A, since the major portion of the compressive force is exerted at that location.

Figure 4:
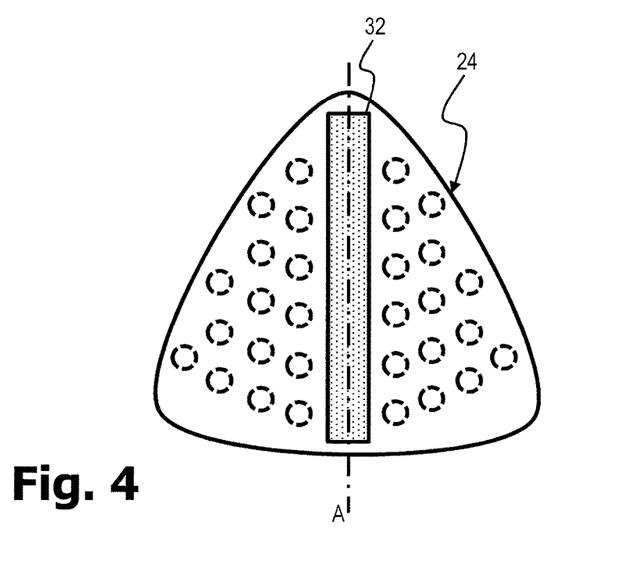
FIG. 4 shows a rear view of the triangular pressure body according to the first embodiment of the invention.

As shown in FIG. 4, a strip 32 made of a material with hooks is firmly attached to the rear side 30 of the pressure body 24 in the area of its center axis A.

Figure 3:
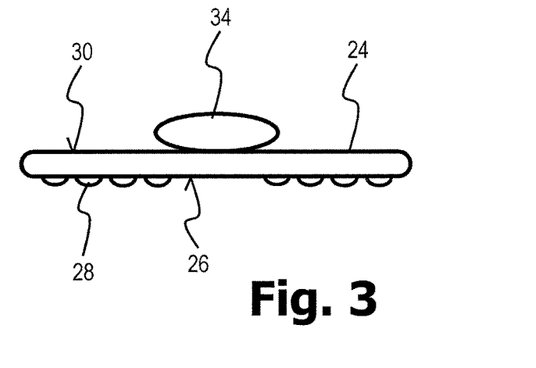
FIG. 3 shows a top view of the triangular pressure body with an elliptical pressure pad according to the first embodiment of the invention.
Figure 5:
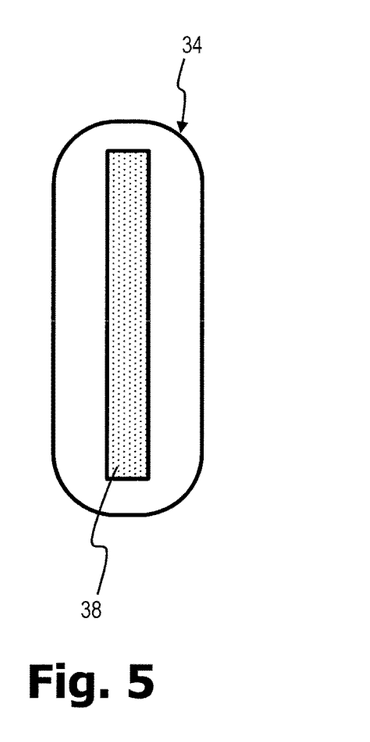
FIG. 5 shows a rear view of the pressure pad according to the first embodiment of the invention.
Figure 6:
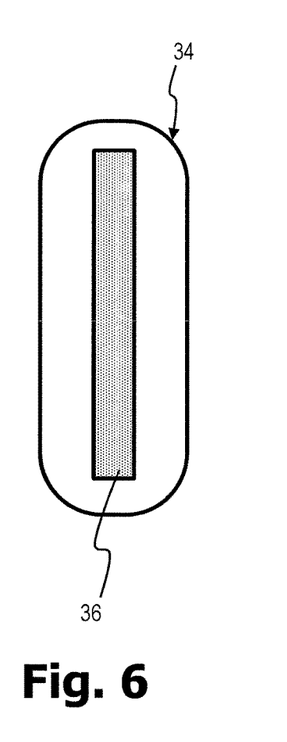
FIG. 6 shows a front view of the pressure pad according to the first embodiment of the invention.
Figure 7A:
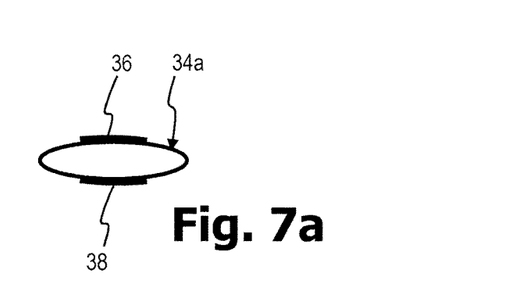
FIGS. 7*a*-7*c* show various top views of the pressure pad for explaining different geometries of pressure pads according to various embodiments of the invention.
Figure 7B:
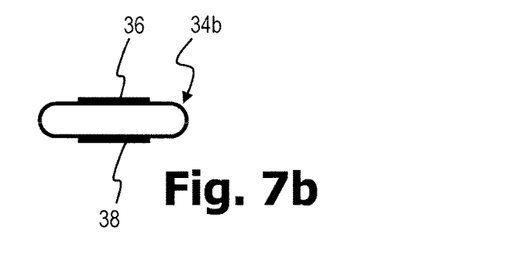
Figure 7C:
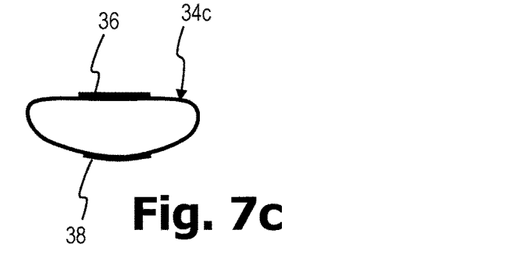

In addition, it is apparent in FIG. 3 that a pressure pad 34 is provided on the rear side 30 of the pressure body 24. Reference is made to FIGS. 5, 6, and 7*a* through 7*c* for explanation of the pressure pad. FIG. 5 shows a rear view of the pressure pad 34, while FIG. 6 shows a front view of the pressure pad 34. FIGS. 7*a* through 7*c* show various geometries of the pressure pad in the top view. The pressure pad 34 is designed as a dimensionally stable, relatively hard elongated silicone body with rounded corners and flattened edge areas. On its front side (FIG. 6) the pressure pad has an area 36 that is provided with loops and that has the approximate dimensions of the area 32 of the pressure body. For attaching the pressure body 24 to the pressure pad 34, the areas 32 and 36 are engaged with one another as a hook and loop fastener. On its rear side, the pressure pad 34 according to FIG. 5 once again has a hook and loop fastener panel 38 that is provided with hooks.

FIGS. 7a through 7c show various possible geometries of the pressure pad. In FIG. 7b, the pressure pad 34a in the top view has an elliptical shape, with the two hook and loop fastener panels 36 and 38 situated on the front side and on the rear side. In the embodiment according to FIG. 7b, the pressure pad 34b has a rounded rectangular shape or an oval shape, with the two hook and loop fastener panels 36 and 38 once again situated on the front side and on the rear side. In the embodiment according to FIG. 7c, the pressure pad 34c has a highly convexly curved shape with the hook and loop fastener panel 38, whereas on its rear side with the hook and loop fastener panel 36 the pressure pad has a flat shape. The hook and loop fastener panel 38 is provided in order for the pressure pad to be fixed to a corresponding hook and loop fastener panel with loops on the inner side 22 of the belt 12, or fixed directly to the inner side 22 of the belt 12 without involvement of a further hook and loop fastener panel.

It is understood that in the subject matter of the present invention, the pressure pad may also have other geometries, regardless of the particular exemplary embodiment. For example, the pressure pad may be shorter, more bulging, or curved more convexly or less convexly, flattened or more curved toward the patient, flattened or more curved toward the rear side, i.e., toward the belt, or more bulging, circular, elliptical, or triangular in the front and rear views.

Figure 8:
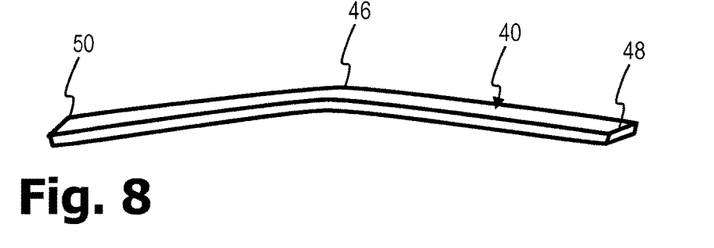
FIG. 8 shows a perspective view of a curved reinforcement element according to the first embodiment of the invention.

FIG. 8 shows a reinforcement element 40. This reinforcement element 40 is provided for mounting in a retaining pocket 42 on the belt 12 (see FIG. 1). The reinforcement element 40 is manufactured from a dimensionally stable material, for example a metal or a hard plastic material such as a thermoplastic material. The retaining pocket 42 is mounted either on the inner side 22 of the belt 12 or on the outer side 44 of the belt 12. In FIG. 1 the retaining pocket is merely indicated by dashed lines, since in the embodiment according to FIG. 1 it is mounted on the outer side 44. The reinforcement element 40 is curved at an angle of approximately 15°. The angle may be selected to be larger or smaller as needed. Due to the curvature, a vertex 46 is formed in the center area of the reinforcement element 40, approximately in the middle area of the belt 12. The orientation of the reinforcement element 40 is provided in such a way that in its end areas 48, 50 it is curved toward the patient, with the vertex 46 pointing away from the patient. Due to this arrangement, the belt may be stabilized via the reinforcement element 40 in the area of the pressure pad 34 in order to better exert pressure on the stomach area of the patient via the pressure pad 34 and ultimately, the pressure body 24.

Figure 9:
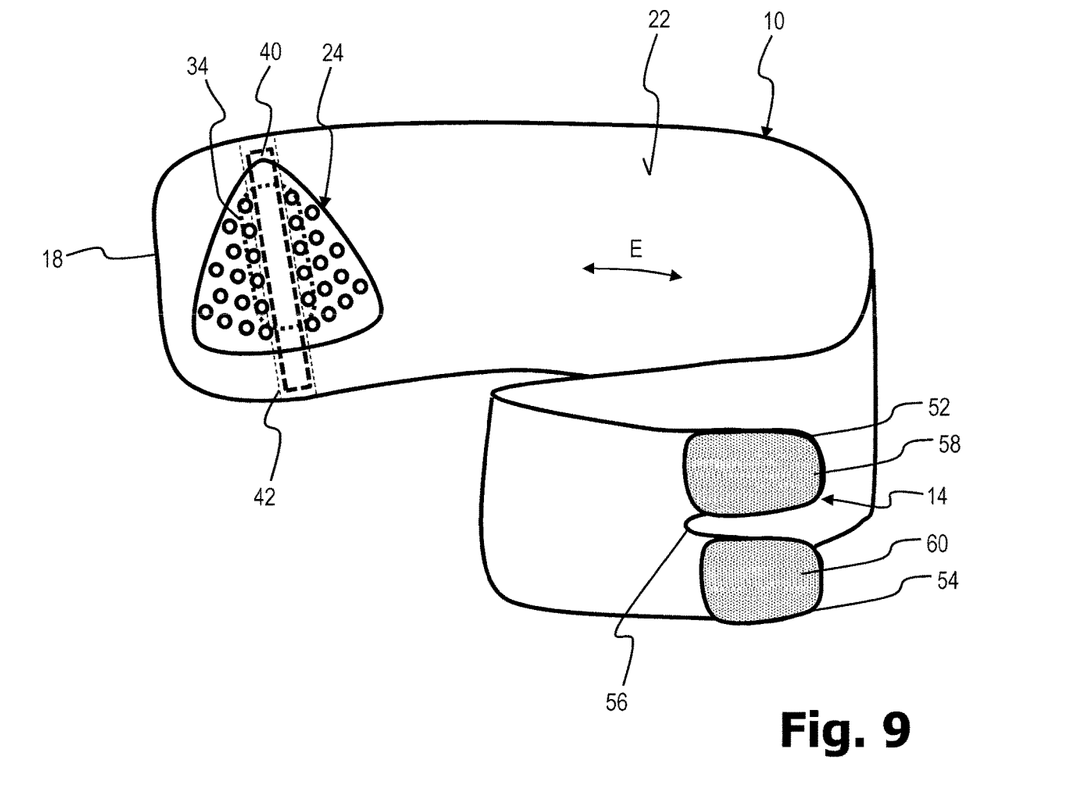
FIG. 9 shows a schematic illustration of a device according to a second embodiment of the present invention.

FIG. 9 shows a second embodiment of the invention which is essentially the same as the first embodiment, but which differs from the subject matter of the first embodiment in the following aspects:

The pressure body 24, the pressure pad 34, the retaining pocket 42, and the reinforcement element 40 are situated near the end 18 of the belt 12.

The other end 14 has two tabs 52 and 54 that are separated from one another by a slot 56.

These tabs 52, 54 have a hook and loop fastener panel 58, 60, respectively, with hooks.

Figure 10:
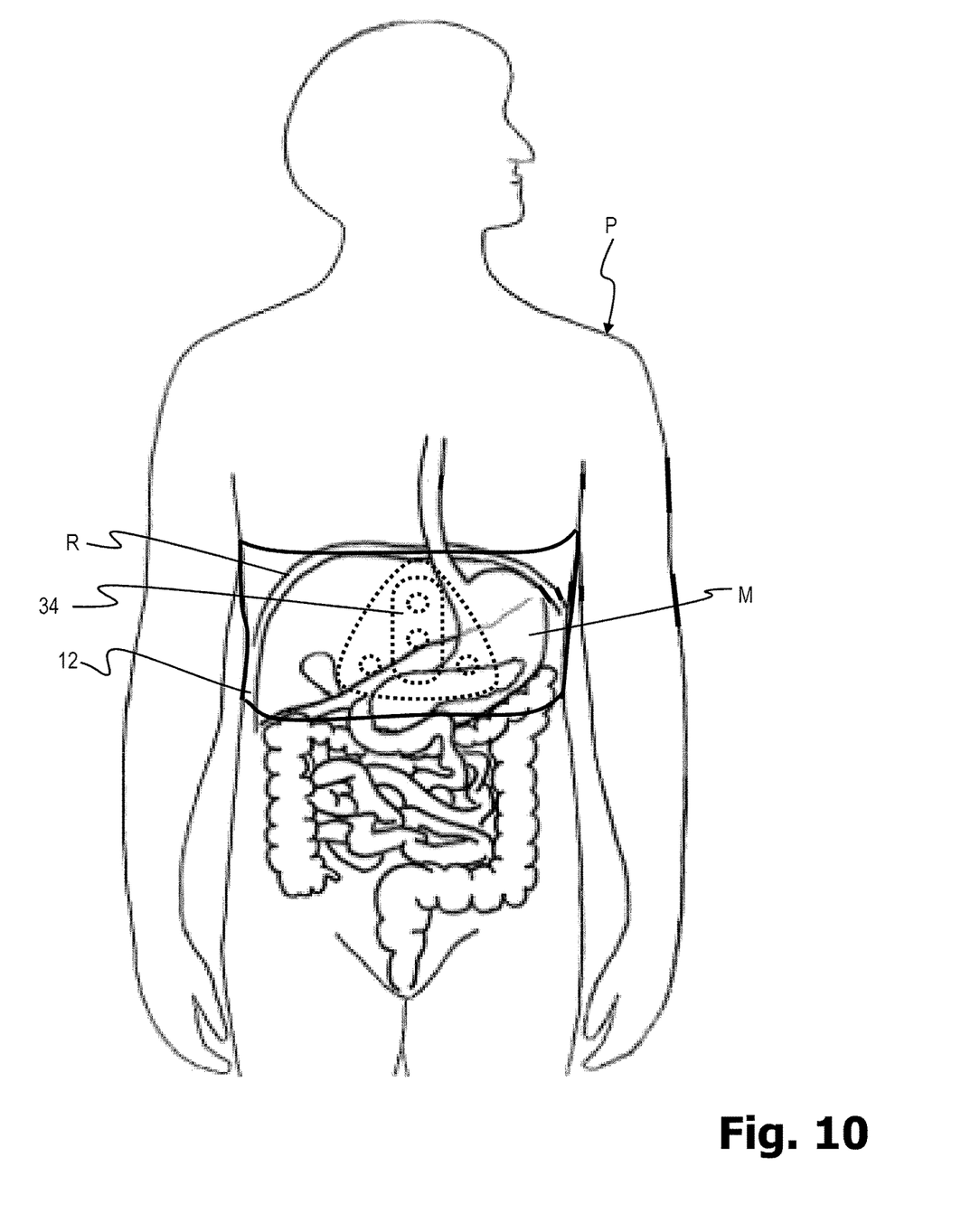
FIG. 10 shows a schematic illustration of a patient to which a device according to the present invention is attached for treatment.

For illustrating the use of the device according to the present invention, FIG. 10 shows a patient P in a schematic illustration, with the organs of the digestive tract being schematically shown in detail. In particular, the illustration of the stomach M is apparent, which is shown in the patient in a slightly enlarged depiction. For reducing the stomach volume, the belt 12 according to the present invention is placed on the patient, and a compressive force is exerted below the costal arch R via the pressure body 24 and the pressure pad 36 in order to reduce the volume that is available for the stomach M. In this way, the patient's feeling of hunger may be effectively reduced on a sustained basis, and excess weight may be effectively controlled.

Figure 11:
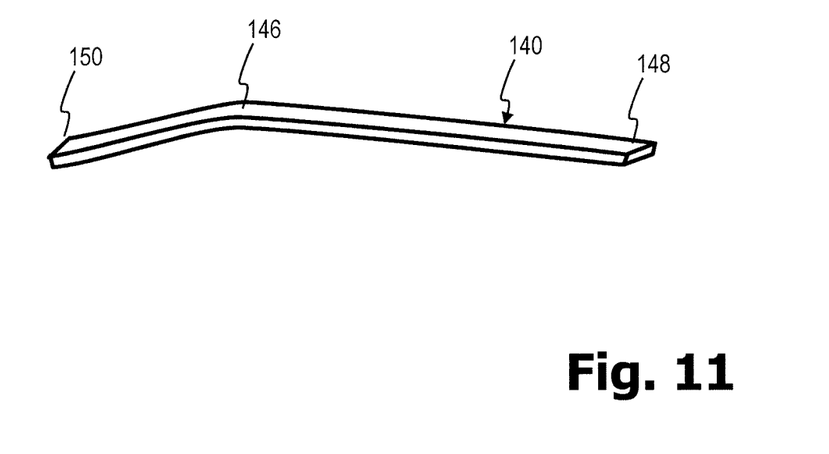
FIG. 11 shows an alternative configuration of a reinforcement element according to a further embodiment of the invention.

FIG. 11 shows an alternative embodiment of a reinforcement element 140, with the vertex 146 situated in an area at the boundary between the first third and the second third of the total length of the reinforcement element. The opening angle is within a range of 150°.

Figure 12:
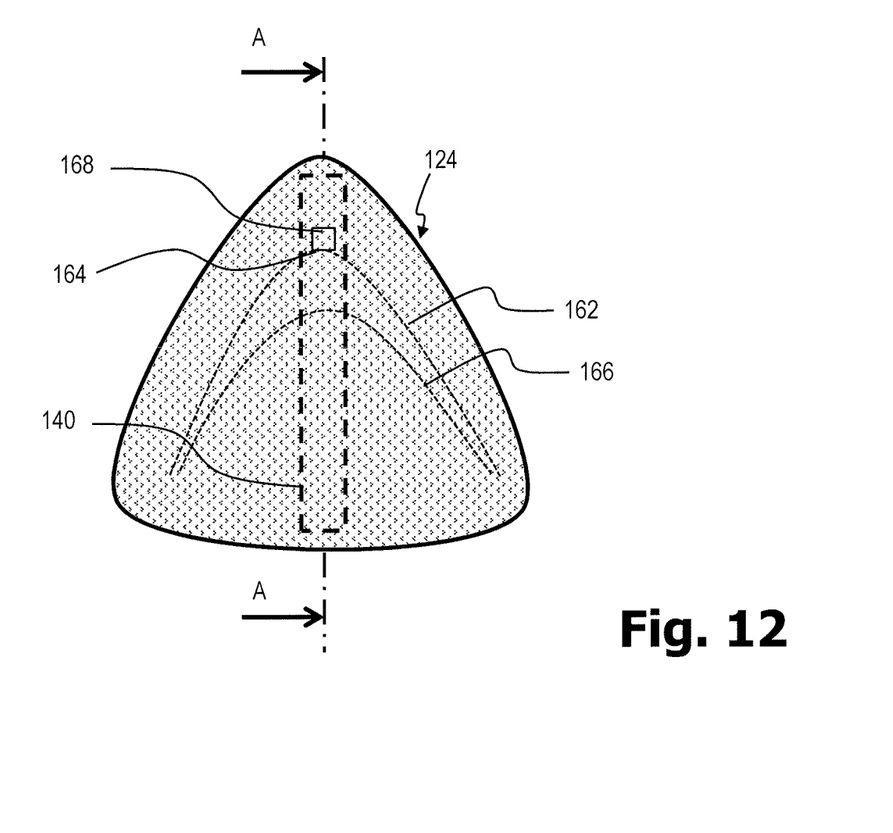
FIG. 12 shows an alternative configuration of a pressure body according to a further embodiment of the invention.

FIG. 12 shows an alternative embodiment of a further pressure body 124. This pressure body is manufactured, for example, from a dimensionally stable rubber material and has a triangular geometry that corresponds to the contour of the human costal arch. The pressure body 124 is coated with a looped material. The contour line 162 may be understood as an elevation line, and in a manner of speaking forms a ridge of a V-shaped elevation that achieves the maximum elevation at its vertex point 164. In addition, a second contour line 166 shows the area of a greatly reduced material thickness of the pressure body 124 below the contour line 162.

A sensor 168 that is used for collecting patient data, for example the pulse and/or heart rate and/or blood pressure and/or blood sugar and/or respiratory rate and/or body temperature and/or fat percentage and/or water percentage and/or muscle percentage and/or body mass index or the like, is provided at the vertex point 164. This sensor 168 is coupleable via a cable-free interface to a user terminal, for example a smart phone, for data transmission.

It is also apparent that the reinforcement element 140 is indicated in FIG. 12.

Figure 13A:
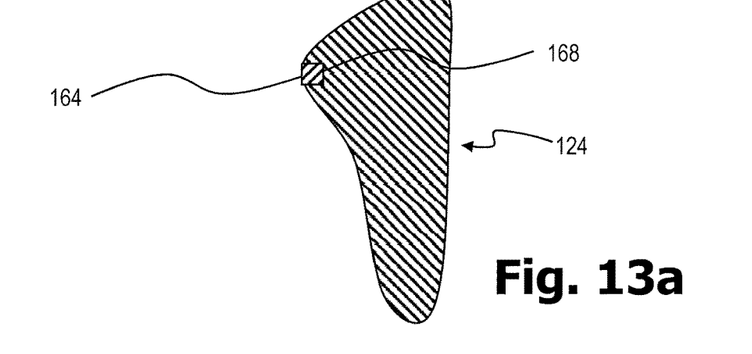
FIGS. 13*a*-13*e* show various possible combinations of the pressure body according to FIG. 12 with the reinforcement element according to FIG. 11.

FIG. 13a shows a cross section of the pressure body 124 along the section line A-A. The solid design made from a deformable foam or rubber material is apparent, which has sufficient dimensional stability to exert pressure on the stomach area of a patient. The area 164 of maximum elevation and the sensor 168 are also apparent. The pressure body 124 is shown without a reinforcement element in the illustration according to FIG. 13a.

FIGS. 13b through 13e show various options for arranging the reinforcement element 140 on the pressure body 124.

Figure 13B:
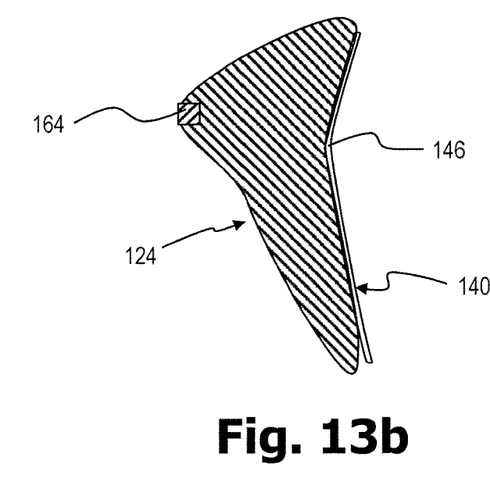

In the arrangement according to FIG. 13b, the reinforcement element 140 is situated with its vertex area 146 in such a way that the vertex 146 presses convexly into the reinforcement element 140 in the area of the maximum elevation 164, and thus provides maximum support to the pressure body 124 for application of compressive force to the stomach area of the patient.

Figure 13C:
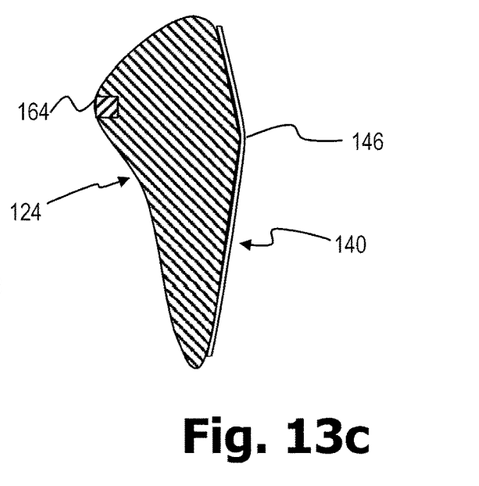

In the arrangement according to FIG. 13c, the reinforcement element 140 is situated with its vertex area 146 in such a way that the vertex 146 lies at approximately the level of the maximum elevation 164 of the pressure body 124 but has a concave arrangement on the pressure body. As a result, the material of the pressure body 124 can yield, in a manner of speaking, in the concave vertex area 146. The application of compressive force to the stomach area of a patient is therefore much less than in the arrangement according to FIG. 13b.

In the arrangement according to FIG. 13c, the reinforcement element 140 is once again provided in a convex arrangement on the pressure body 124, but the vertex area 146 is situated considerably below the area of the maximum elevation 164. As a result, the application of compressive force to the stomach area of the patient is less than for the state according to FIG. 13*d*.

Figure 13D:
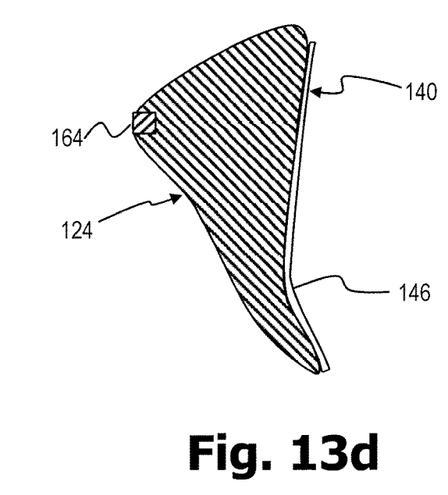
Figure 13E:
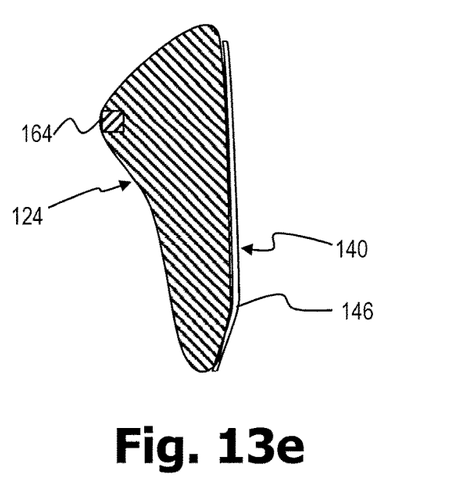

In the arrangement according to FIG. 13*e*, the reinforcement element 140 is rotated by 180° with respect to the state in FIG. 13*d*, once again resulting in a concave arrangement of the vertex area 146. The application of compressive force to the stomach area of the patient is thus further reduced due to the fact that material of the pressure body 124 can yield in the vertex area 146.

As a whole, the different options for arranging the pressure body 124 and the reinforcement element 140 result in various variation options for setting the compressive force that is exerted on the stomach area of the patient. Thus, for example, within the scope of one treatment, by changing the arrangement of the reinforcement element 140, initially less, and subsequently more, pressure may be exerted on the stomach area in order to control the course of treatment, for example with a gentle start of treatment, using a small compressive force on the stomach area, followed by a stepwise increase in the application of compressive force.

The invention claimed is:

1. A device for externally applying a local compressive force below a costal arch of a patient for reducing a volume of a stomach, comprising:
   an elastic belt that is placeable, under tensile stress, around an upper body of a patient in an area of the costal arch, and
   a pressure body that is attachable to the elastic belt and designed in such a way that the pressure body exerts a compressive force on the stomach inside the patient according to the tensile stress of the elastic belt,
   wherein a geometry of the pressure body designed in a shape of a rounded triangle such that it is adapted to an anatomy of the costal arch and fits snugly therein; wherein the pressure body is designed with an elevation area having an inverted V shape, and having its greatest material thickness proximate a vertex of the V.

2. The device according to claim 1, wherein the elastic belt is closed or designed in a form of an at least partially elastic band, which in an area of its ends may be joined together via a connector to adjust its effective length around an upper body of the patient.

3. The device according to claim 2, wherein the connector is designed in a form of a hook and loop fastener.

4. The device according to claim 1, wherein the pressure body is designed in a form of a flat, flexible pressure body.

5. The device according to claim 4, wherein a surface of the pressure body contacting the patient is provided with protruding knobs.

6. The device according to claim 4, wherein a fastener is provided on a rear side of the pressure body.

7. The device according to claim 1, wherein a pressure pad is provided between the pressure body and an inner side of the elastic belt intended to contact the patient.

8. The device according to claim 7, wherein the pressure pad is made of a dimensionally stable, preferably elastic, material, preferably rubber, plastic, or silicone.

9. The device according to claim 7, wherein the pressure pad has a convex shape at least on one side, wherein the pressure pad has a rectangular, rounded rectangular, elliptical, or oval cross section.

10. The device according to claim 7, wherein the pressure pad has a fastener on its side facing the elastic belt and on its side facing the pressure body.

11. The device according to claim 7, wherein the pressure body is covered with a looped material, the looped material being formed directly on the pressure body or designed as a replaceable fabric pocket that accommodates the pressure body.

12. The device according to claim 7, wherein the elastic belt is attachable in an area in which the pressure body is reinforced by a reinforcement element, wherein the reinforcement element is dimensionally stable.

13. The device according to claim 12, wherein an area in which the pressure body is attachable, is situated in a middle section or in an end area of the elastic belt.

14. The device according to claim 12, wherein the elastic belt has a retaining pocket for accommodating the reinforcement element.

15. The device according to claim 12, wherein the reinforcement element is formed by a curved, arch-shaped reinforcement strip comprising two end areas and a middle area, wherein the two end areas protrude with respect to the middle area, the reinforcement element being accommodated in the elastic belt or mounted thereon in such a way that the two end areas protrude in a direction of contact with the patient.

16. The device according to claim 15, wherein the reinforcement element has a rounded vertex area that is situated off-center, the reinforcement element in its vertex area having an opening angle of 170° to 120°.

17. The device according to claim 16, wherein the reinforcement element is selectively providable in a convex or concave arrangement relative to the pressure body, or selectively providable with its vertex area near or far from a maximum material thickness of the pressure body.

18. The device according to claim 1, wherein at least one sensor for detecting patient parameters, is provided in the elastic belt in an area that is in contact with skin of the patient, in particular in the pressure body, wherein the sensor is coupleable to a data transmission terminal via a cabled or cable-free connection, for example via IR, Bluetooth, Wi-Fi, or a mobile radio connection.

* * * * *